United States Patent [19]

Fiese et al.

[11] Patent Number: 4,785,078
[45] Date of Patent: Nov. 15, 1988

[54] TRANSFORMATION PRODUCT OF THIOSPORAMICIN

[75] Inventors: Eugene F. Fiese, Ledyard; Charles E. Moppett, Mystic; Wendell W. Windisch, Groton, all of Conn.

[73] Assignee: Pfizer Inc., New York, N.Y.

[21] Appl. No.: 938,083

[22] PCT Filed: Apr. 18, 1985

[86] PCT No.: PCT/US85/00698

§ 371 Date: Nov. 20, 1986

§ 102(e) Date: Nov. 20, 1986

[87] PCT Pub. No.: WO86/06065

PCT Pub. Date: Oct. 23, 1986

[51] Int. Cl.$^4$ .................. C07K 7/52; A61K 35/00
[52] U.S. Cl. ................................. 530/317; 424/117
[58] Field of Search ................... 424/117; 530/317

[56] References Cited

U.S. PATENT DOCUMENTS 2,982,689  5/1961  Donovick et al. ............... 424/117
3,761,587  9/1973  Miyairi et al. .................. 424/117
4,083,963  4/1978  Celmer et al. .................. 424/117
4,175,126  11/1979 Lombardi et al. ............... 424/117
4,293,489  10/1981 Debono .......................... 260/112.5 R
4,320,052  3/1982  Abbott et al. .................. 260/112.5 R

OTHER PUBLICATIONS

Pagano et al., Antibiotics Annual, pp. 554–559 (1955/6).
Nishimura et al., The Journal of Antibiotics, Ser. A., vol. XIV, No. 5, pp. 255–263 (Sep. 1961).
Miyairi et al., The Journal of Antibiotics, vol. XXIII, No. 3, pp. 113–119 (Jan. 1970).
Thiemann et al., The Journal of Antibiotics, vol. XXI, No. 9, pp. 525–531 (Sep. 1968).
Kondo et al, Studies of a New Antibiotic Produced by Streptomyces Sp. A-59, J. Ant. A14=194–198, 1961.

Primary Examiner—Ronald W. Griffin
Assistant Examiner—A. Mohamed
Attorney, Agent, or Firm—Peter C. Richardson; Lawrence C. Akers; Paul H. Ginsburg

[57] ABSTRACT

A new sulfur-containing polypeptide antibiotic produced by the hydrolysis of thiosporamicin (CP-46,192) is useful for the improving feed utilization efficiency in poultry and swine.

5 Claims, No Drawings

TRANSFORMATION PRODUCT OF THIOSPORAMICIN

TECHNICAL FIELD

This invention is concerned with a new member of the sulfur-containing polypeptide group of antibiotics.

BACKGROUND ART

This family of antibiotics includes thiostrepton (Antibiotics Ann., 1955–1956, 554–559); siomycin (J. Antibiotics, 14:255, 1961): A-59 (J. Antibiotics, A14:194, 1961); thiopeptin (J. Antibiotics, 23:113–119, 1970); sporangiomycin (J. Antibiotics, 21:525–531, 1968); and CP-46, 192, U.S. Pat. No. 4,083,963.

DISCLOSURE OF THE INVENTION

This invention is concerned with a new sulfur-containing polypeptide antibiotic of the formula

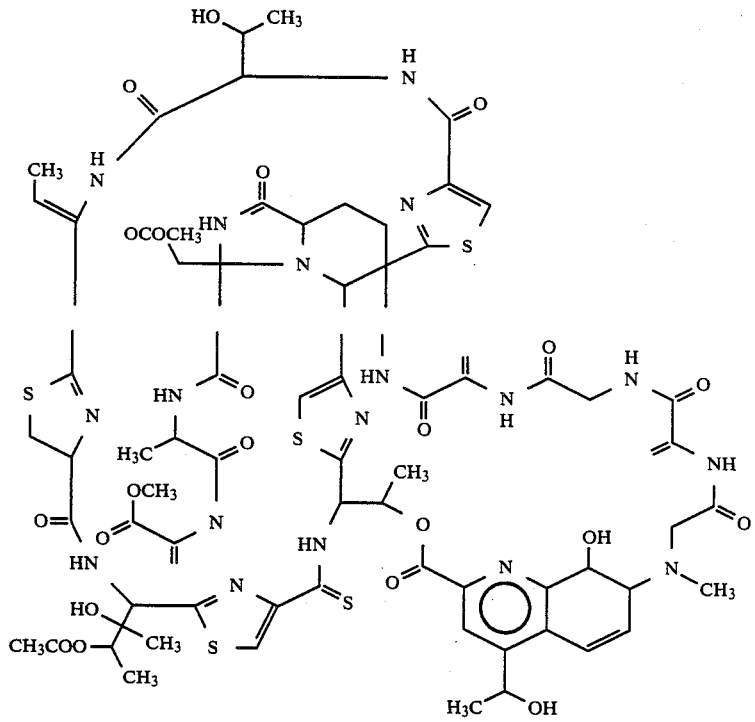

known as CP-53,648.

The present invention also provides a process of preparing CP-53,648 by hydrolyzing thiosporamicin i.e. the compound of the formula

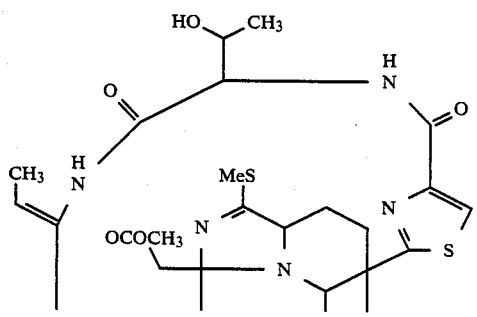

-continued

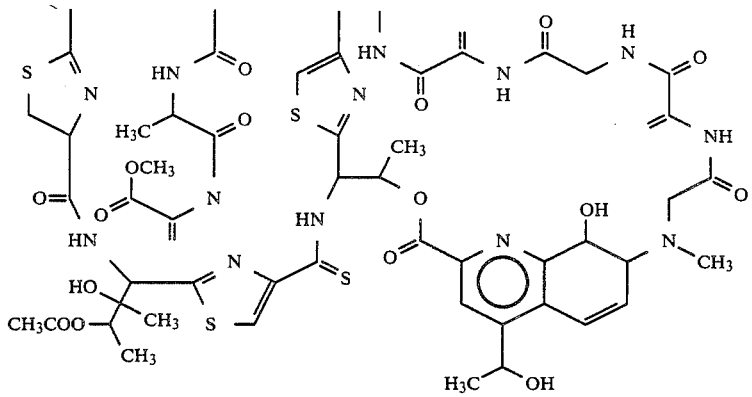

under acid conditions.

Additionally the present invention provides for a method of promoting growth of poultry and swine and for increasing the feed utilization efficiency thereof by orally administering a growth and feed utilization efficiency promoting amount of CP-53,648. The invention also embraces feed compositions suitable for ingestion by poultry and swine comprising a nutritionally balanced, growth and feed utilization, efficiency-promoting amount of CP-53,648, together with a physiologically acceptable carrier or diluent.

DETAILED DESCRIPTION

The antibiotic compound of the present invention, CP-53,648, is formed by the acid hydrolysis of thiosporamicin.

The starting material, thiosporamicin was originally isolated from soil samples found in Canada and France, and on examination was found to have the morphological features of a Streptosporangium. This genus is differentiated from others belonging to the group actinomycetes by the production of coiled chains of round elliptical spores contained in sporangia and the production of aerial mycelium on the surface of the culture.

The preparation of the starting material thiosporamicin, also known as Antibiotic Compound 46,192 is described in U.S. Pat. No. 4,083,963.

The novel compound of the present invention is prepared by acid hydrolysis of thiosporamicin. In a preferred embodiment a solution of thiosporamicin is treated with an aqueous solution of either a buffered mineral acid or an acid salt. Suitable mineral acids include hydrochloric acid and phosphoric acid. A suitable acid salt is for example, cobalt chloride. Preferably the thiosporamicin is first dissolved in a solvent such as acetonitrile. Other suitable solvents include dimethyl sulfoxide.

It is important that the required acidic conditions be maintained for the reaction to proceed efficiently. The pH of the reaction mixture is maintained at from about 1.0 to 5.0 preferably from about 3.5 to 4.2. If necessary the pH of the reaction mixture can be maintained by the addition of, for example, phosphoric acid. Other suitable acids include hydrochloric acid.

The mixture of the aqueous acid solution and the thiosporamicin is heated for about 2 to 50 hours, preferably 10 to 48 hours at a temperature from about 40° to 50°. The resulting product can be collected by conventional means, for example extraction with an organic solvent. The product is preferably purified by chromatography.

CP-53,648 is active against a variety of Gram-positive bacteria as illustrated in Table 1.

TABLE I

| Organism | Minimum Inhibitor Concentration (mcg/ml) |
| --- | --- |
| *Staphylococcus, aureaus* sp. | 1.56 |
| *Streptococcus equi.* | .006 |
| *Streptococcus agalac.* | .049 |

Significant parenteral protection is afforded to mice experimentally infected with *Staphylococcus aureus* 01A005 by Compound CP-53,648 at doses of 50 to 200 mg./kg. and an oral dose of 200 mg./kg.

Crude antibiotic mixtures such as those obtained directly from the reaction broth or in any of the intermediate recovery stages as well as purified Compound CP-53,648 may also be employed in the treatment of antibiotic sensitive infections in man and animals at parenteral doses of 200 to 1000 mg., depending on the type and severity of the infection and weight of the subject being treated. Solutions of Compound CP-53,648 in sesame oil, peanut oil and/or propylene glycol at concentrations of 200 to 500 mg./ml. may be employed for subcutaneous or intramuscular administration.

Improvement of feed utilization by monogastric animals such as horses, pigs, chickens, and rabbits may be obtained with the incorporation of Compound CP-53,648 in animal feeds. Pure Compound CP-53,648 and the crude isolated compound may be incorporated in feed compositions at the desired potency concentration.

The compounds of the present invention can be administered either orally or parenterally, but because of their oral activity, they are conveniently administered by adding to the feed supplied to the animals. The compound may be added to a supplementary feed, or to all or part of the daily feed ration. In practice, addition to the normal mixed feed is preferred because of its greater convenience.

Conventional animal feeds may be used containing, for example, cereals such as maize, corn, wheat or barley; protein sources such as fish or meat by-products; fats; vitamins and minerals; each in an amount sufficient to meet the nutritional requirements of the animals in accordance with standard veterinary practice.

One particular application in which the compounds of the present invention have been found to be especially beneficial is in improving the efficiency of feed utilization and promoting growth in poultry, especially chickens. In this instance the compounds of the invention are added to the feed to give a feed utilization improving and growth promotant amount of between 1 ppm and 20 ppm of feed, most preferably between 2 ppm. and 10 ppm. The feed is normally provided to the poultry on a free-access basis from shortly after hatching, (e.g., as day-old chicks), until shortly before slaughter, thereby providing continuous administration of compound throughout the growth of animals.

Because of the low levels of additive needed the compound of the present invention is extremely economical. Moreover, while it is possible to administer the compound on a continuous basis in the feed as described above, it is also possible to administer the compound intermittently, or at specific periods during the growth of the animals.

The following examples are solely for the purpose of illustration and are not to be construed as limitations of this invention, many variations of which are possible without departing from the spirit or scope thereof.

EXAMPLE I

An aqueous solution of 300 ml. of 5% disodium hydrogen phosphate previously adjusted to pH 3.5 with 85% phosphoric acid, was added to a stirring solution of 30 grams of pure thiosporamicin the starting material in 600 ml. acetonitrile. The pH of the mixture was adjusted from 4.2 to 3.5 with 85% phosphoric acid and heated in an oil bath to 55° C. for 48 hours. Methyl mercaptan was given off as a gaseous by-product.

The pH of the reaction was maintained at 3.5 by adding 85% phosphoric acid as needed. At the termination of the reaction 300 ml. of saturated sodium chloride was added and the organic phase separated, evaporated and dried for 20 hours producing 29.5 grams of a solid.

The product was purified by passing it through a chromatography column filled with 1 kg. silica gel 60 (230–400 mesh) packed in methylene chloride and eluted with a gradient of acetone/methylene chloride. The starting material 16 grams eluted first followed by 9.1 grams of the desired product CP 53,648.

The resulting antibiotic P-53,648 when in the crystalline form has a melting point of 217°–222°; has absorption maxima in methanol in the ultraviolet light region of the spectrum at 240 and 290 nm with values of 54,200 and 15,600, respectively; has the average composition by weight of 50.05% carbon, 5.10% hydrogen, 14.09% nitrogen and 8.95% sulfur; and as a 1% solution in chloroform exhibited its characteristic absorption in the infrared region at the following wavelengths: 3400, 3325, 1735, 1660, 1485, 1380, 1330, 1170, 1060, 1,020 and 890 in $cm^{-1}$.

EXAMPLE II

A solution of 1.0 gram pure thiosporamicin in 20 ml. acetonitrile was added to 10 ml. of 2% cobalt chloride solution (initial pH of 4.2) and the solution was heated at 55° C. for 32.5 hours. The pH at the end was 2.9. The pH was adjusted to 7.0 with 1N sodium hydroxide and the solution was evaporated in vacuo to a solid. The addition of 20 ml. water followed by stirring for 20 minutes and filtration produced 680 mg. of dry crude reaction product. This solid was stirred in 20 ml. of chloroform for 20 minutes and insoluble salts removed. Evaporation of the solvent and chromatography of the resultant solid yielded CP-53,648.

EXAMPLE III

A solution of 30 grams of thiosporamicin in 2000 ml. acetonitrile and 0.1N hydrochloric acid was heated for 4 hours at 37° C. At reaction end the pH was raised to 7.0 by the addition of 10N sodium hydroxide. The mixture was concentrated in vacuo until a solid precipitated. After standing 16 hours, the solid was collected on a celite pad. The reaction was repeated four more times.

The combined solids and diatomaceous earth were heated with 400 ml. chloroform to reflux and filtered. Concentration of the filtrate yielded 15.4 g. of crude reaction product.

3.5 grams of the product was purified by medium pressure chromatography using a 25×1000 mm. column packed with 370 grams of silica gel 60 (230–400 mesh) in acetone/chloroform in 5:95 v/v. Gradient elution gave 1.2 grams of the compound CP-53,648.

Administration of the Compound CP-53,648 in chick feed produced significant increase in weight. The results for 21 days, and 28 days are given in the following Table.

| Compound | LIVE WEIGHT (21 days) | | | LIVE WEIGHT (28 days) | | |
| --- | --- | --- | --- | --- | --- | --- |
| | Dose ppm feed | Mean weight (g) | % Diff. from Control | Dose ppm feed | Mean weight (g) | % Diff. from Control |
| NONE (Control | — | 447 | — | — | 643 | — |
| CP 53,648 | 10 | 478 | 6.8 | 10 | 692 | 7.6 |
| CP 53,648 | 5 | 461 | 3.1 | 5 | 681 | 6.0 |
| CP 53,648 | 1 | 467 | 4.4 | 1 | 671 | 4.4 |

We claim:

1. A Compound CP-53,648 of the formula

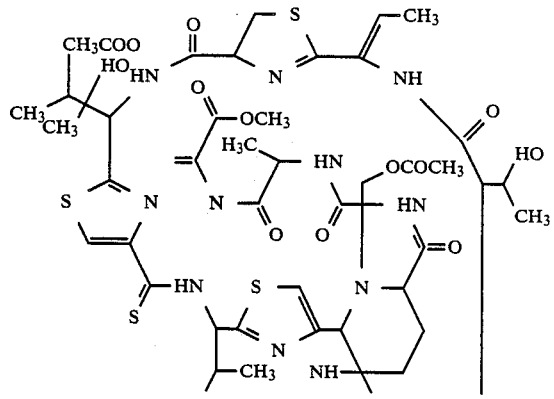

-continued

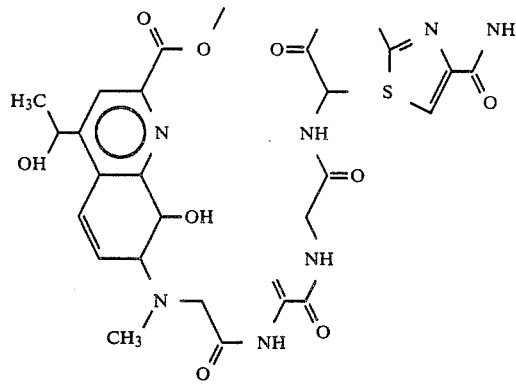

2. The compound of claim 1 in essentially pure form.

3. A feed composition containing an effective amount of the compound of claim 1 and a nutritionally balanced animal feed.

4. A method for promoting growth of poultry or swine and for increasing the feed utilization efficiency thereof which comprises orally administering to said poultry and swine a growth promoting and feed utilization efficiency promoting amount of a compound of claim 1.

5. A method according to claim 4 wherein said compound is added to feed ingested by the poultry and swine.

* * * * *